(12) United States Patent
Azimi

(10) Patent No.: US 9,183,353 B2
(45) Date of Patent: Nov. 10, 2015

(54) SYSTEM FOR REAL-TIME TRACKING OF MEDICATION USE BY A USER

(71) Applicant: DynoSense, Corp., Sunnyvale, CA (US)

(72) Inventor: Saeed Azimi, Los Gatos, CA (US)

(73) Assignee: DynoSense, Corp., Sunnyvale, CA (US)

( * ) Notice: Subject to any disclaimer, the term of this patent is extended or adjusted under 35 U.S.C. 154(b) by 94 days.

(21) Appl. No.: 14/028,527

(22) Filed: Sep. 16, 2013

(65) Prior Publication Data

US 2015/0081316 A1    Mar. 19, 2015

(51) Int. Cl.
*G06Q 10/00* (2012.01)
*G06F 19/00* (2011.01)

(52) U.S. Cl.
CPC .................................. *G06F 19/3462* (2013.01)

(58) Field of Classification Search
None
See application file for complete search history.

(56) References Cited

U.S. PATENT DOCUMENTS

| 6,317,390 | B1 | 11/2001 | Cardoza |
| 6,667,936 | B1 | 12/2003 | Ditzig |
| 6,845,064 | B2 | 1/2005 | Hildebrandt |
| 7,138,906 | B2 | 11/2006 | Rosche |
| 7,382,692 | B1 | 6/2008 | Hildebrandt |
| 7,907,477 | B2 | 3/2011 | Puzia |
| 2014/0372144 | A1* | 12/2014 | Sterns et al. ...................... 705/2 |

* cited by examiner

*Primary Examiner* — Michelle L Le
(74) *Attorney, Agent, or Firm* — Plager Schack LLP

(57) ABSTRACT

A system for tracking the use of medication by a user in real-time generates data pertaining to the medication use including time of consumption and amount of medication available, and transmit the data to a network so the data is readily accessible to at least one party of interest. The system includes a base unit housing affixed to a cover for use with a medication container, the base unit housing having a micro-electro-mechanical system able to detect motion of the cover and determine when the user removes the cover from the medication container, a computing device to generate the medication use data based on information from the micro-electro-mechanical system, and a communication system to transmit the medication use data to a cloud computer via the network, thereby providing the at least one party of interest access to the cloud computer and the medication use data.

11 Claims, 4 Drawing Sheets

SYSTEM FOR REAL-TIME TRACKING OF MEDICATION USE BY A USER

BACKGROUND

The embodiments herein relate generally to the field of tracking medication use of a user. More specifically, embodiments of the invention relate to a system for tracking medication usage and providing alerts, notifications and reports on such usage to parties of interest such as care-givers, nurses, doctors, pharmacists and family members.

Research has shown that errors occur when patients take a prescribed medicine. This is a common occurrence for elderly patients and/or people suffering from a mental illness. Such errors may lead to overdosing if the medication is taken too early or under dosing if the medication is not taken within the proper time frame. There is a further need in the industry to recognize when a user's medication needs to be refilled so there is no interruption in the medication use. Physicians would also like to know if prescribed medication has been taken correctly by the user to better assess the effectiveness of a prescribed dosage. In clinical settings or managed-care facilities and hospital settings, administrators are required to be vigilant about medication dosages, especially in non-intensive facilities where medication usage is left to individual patients or less skilled care-givers.

There exists a variety of systems for tracking medication use by a user through the use of alarms and/or timers that are placed on a medication bottle cap, such as U.S. Pat. Nos. 6,317,390, 7,138,906, 7,382,692, 6,845,064, 6,667,936 and 7,907,477. However, these systems are limited because they do not generate data regarding the user's consumption of the medicine in the bottle, which is then transmitted via a network to other parties of interest.

As such, there is a need in the industry for a system for the real-time tracking of medication use by a user, which generates data pertaining to the medication use and transmits the data to a network so that the data may be readily accessible to parties of interest.

SUMMARY

A system for tracking the use of medication by a user in real-time is provided. The system is configured to generate data pertaining to the medication use including time of consumption and amount of medication available and transmit the data to a network so the data will be readily accessible to at least one party of interest. The system comprises a base unit housing configured to be affixed to a cover for use with a medication container, the base unit housing comprising a micro-electro-mechanical system configured to detect motion of the cover and determine when the user removes the cover from the medication container, a computing device configured to generate the medication use data based on information from the micro-electro-mechanical system, and a communication system configured to transmit the medication use data to a cloud computer via the network, thereby providing the at least one party of interest access to the cloud computer and the medication use data.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
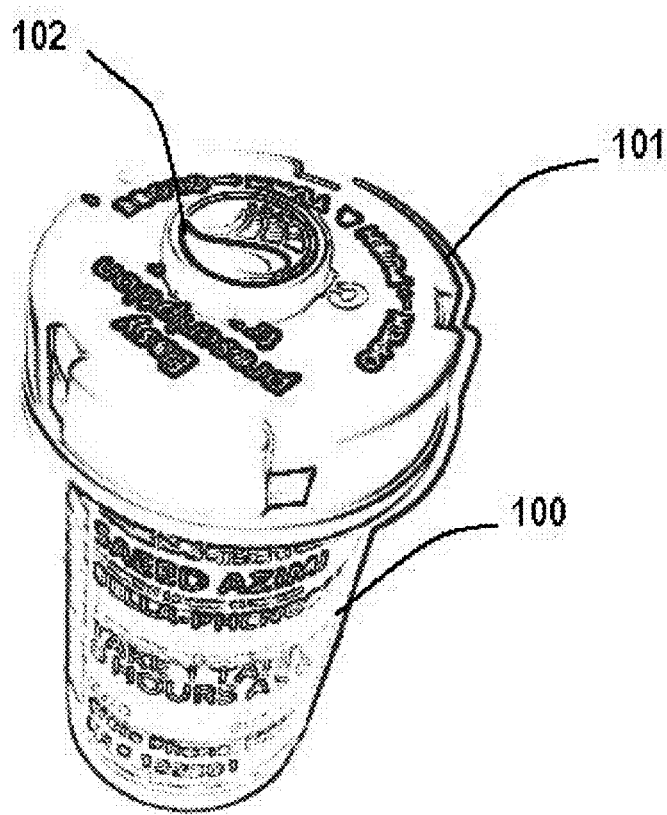
FIG. 1 depicts a perspective view of one embodiment of the invention.

As depicted in FIG. 1, the medication use tracking system comprises device 102 configured to be affixed to medication cap 101 of medication bottle 100. The device 102 has a disposable plastic housing in the shape of a disk having a diameter less than 20 millimeters and a thickness of less than 5 millimeters. Device 102 may be affixed to medication cap 101 using any adhesive known in the field such as glue.

Figure 2:
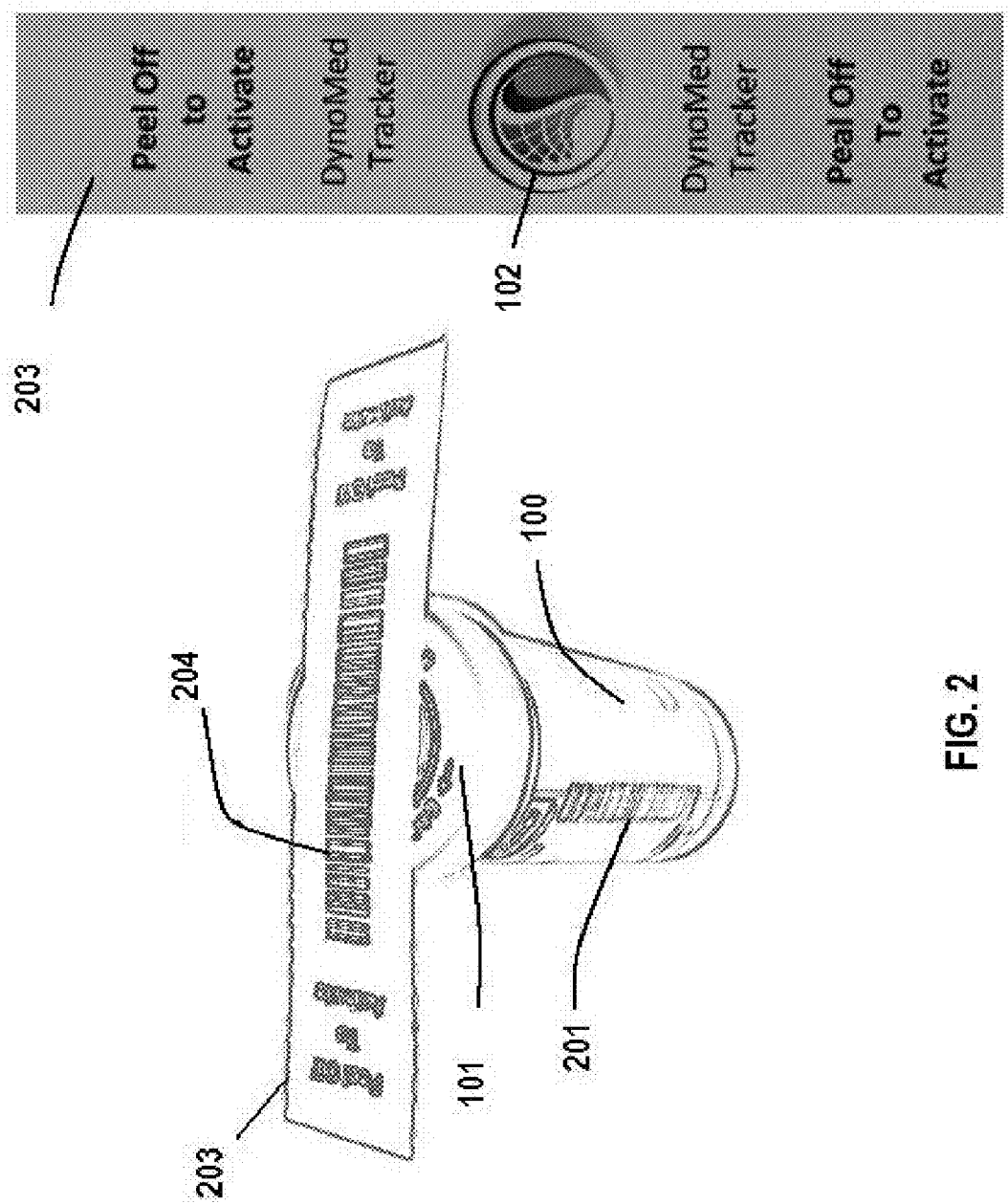
FIG. 2 depicts a perspective view of one embodiment of the invention.

As depicted in FIG. 2, in one embodiment, one side of device 102 is attached to rectangular paper strip 203 by an adhesive. The other side of device 102 is attached to medication cap 101. Paper strip 203 may contain a barcode 204, which contains a preprogrammed unique ID that is assigned to device 102. Medication bottle 100 contains a label, which may include medication information including, but not limited to, patient name, medication name and medication usage requirements such as the frequency and quantity in which the medication should be consumed by the user. Medication bottle 100 also contains barcode 201 on the label, which may contain all of the information printed on the label.

Figure 3:
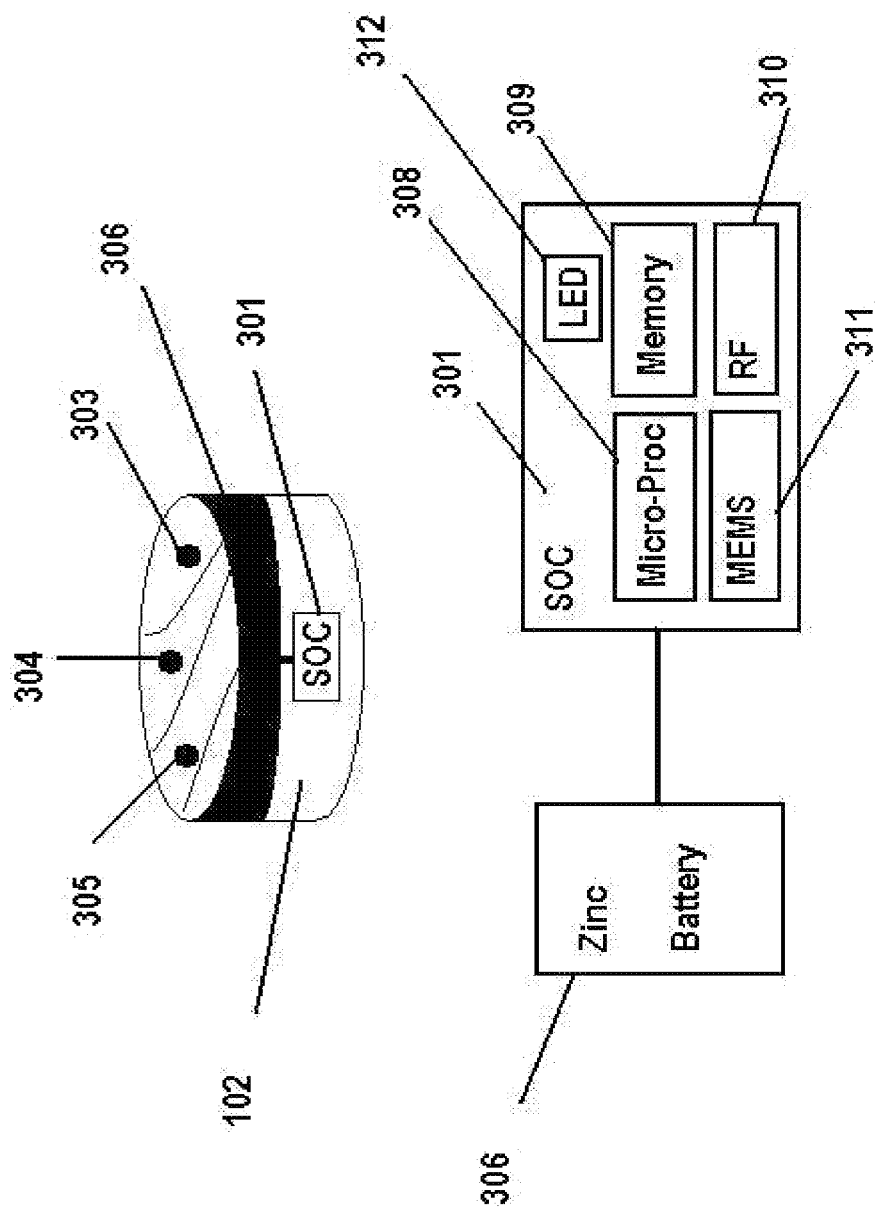
FIG. 3 depicts a perspective view of one embodiment of the invention and a block diagram of several components of the system in accordance with certain embodiments.

As depicted in FIG. 3, device 102 is shown in more detail. Device 102 comprises apertures 303, 304 and 305 on the housing, and zinc battery 306 connected to System-On-Chip ("SOC") 301 electronics within the housing. Zinc-air batteries are non-rechargeable batteries powered by oxidizing zinc with oxygen from the air. These batteries have high energy densities and are inexpensive to produce. These batteries are also beneficial because they have a low profile, are environmentally safe and operate only when exposed to air, which enables them to have a long shelf life when they are not exposed to air. Device 102 and System-On-Chip 301 will be powered by zinc-battery 306, when the battery receives sufficient oxygen through apertures 303, 304 and 305 to interact with the zinc to generate electricity. Paper strip 203 is used to seal apertures 303, 304 and 305 and prevent the flow of oxygen to zinc-battery 306 until it is time to remove the strip and activate the battery.

System-On-Chip 301 electronics has integrated microprocessor unit 308, embedded algorithmic instructions and programs stored on memory unit 309, Micro-Electro-Mechanical Systems ("MEMS") 311 for motion sensing of device 102, and radio frequency system ("RF") 310 to communicate wirelessly with external relay devices or mobile computing devices, and light-emitting diode 312.

Micro-Electro-Mechanical Systems 311 is a technology that in its most general form can be defined as miniaturized mechanical and electro-mechanical elements (i.e., devices and structures) that are made using the techniques of microfabrication used for making transistors that create all electronic logic gates. These devices are able to detect motion in all three 3 axes (X, Y, and Z) with great precision. The components of MEMS 311 are cost effective and are easily integrated with other electronic components in System-On-Chip 301.

Microprocessor unit 308 acts as a local computing device on SOC 301 and acquires motion information from MEMS 311. Using the motion information, microprocessor 308 determines whether medication cap 101 has been opened or closed by running the algorithmic instructions and programs stored on memory unit 309. A timestamp including day and/or time is associated with each open and/or close of medication cap 101 with respect to medication bottle 100. This medication use data, including the motion information pertaining to cap 101 and timestamp data, may be stored to memory unit 309. RF system 310 identifies if it is in the vicinity of a radio receiving device that can receive and/or transmit information pertaining to the medication use data via a network. This type of query is well defined in all standard wireless protocols in use today such as BlueTooth Radio (IEEE 802.15) or WiFi (IEEE 802.11). IEEE is the Institute of Electrical and Electronics Engineers, a professional organization dedicated to creating these electronic standards.

Figure 4:
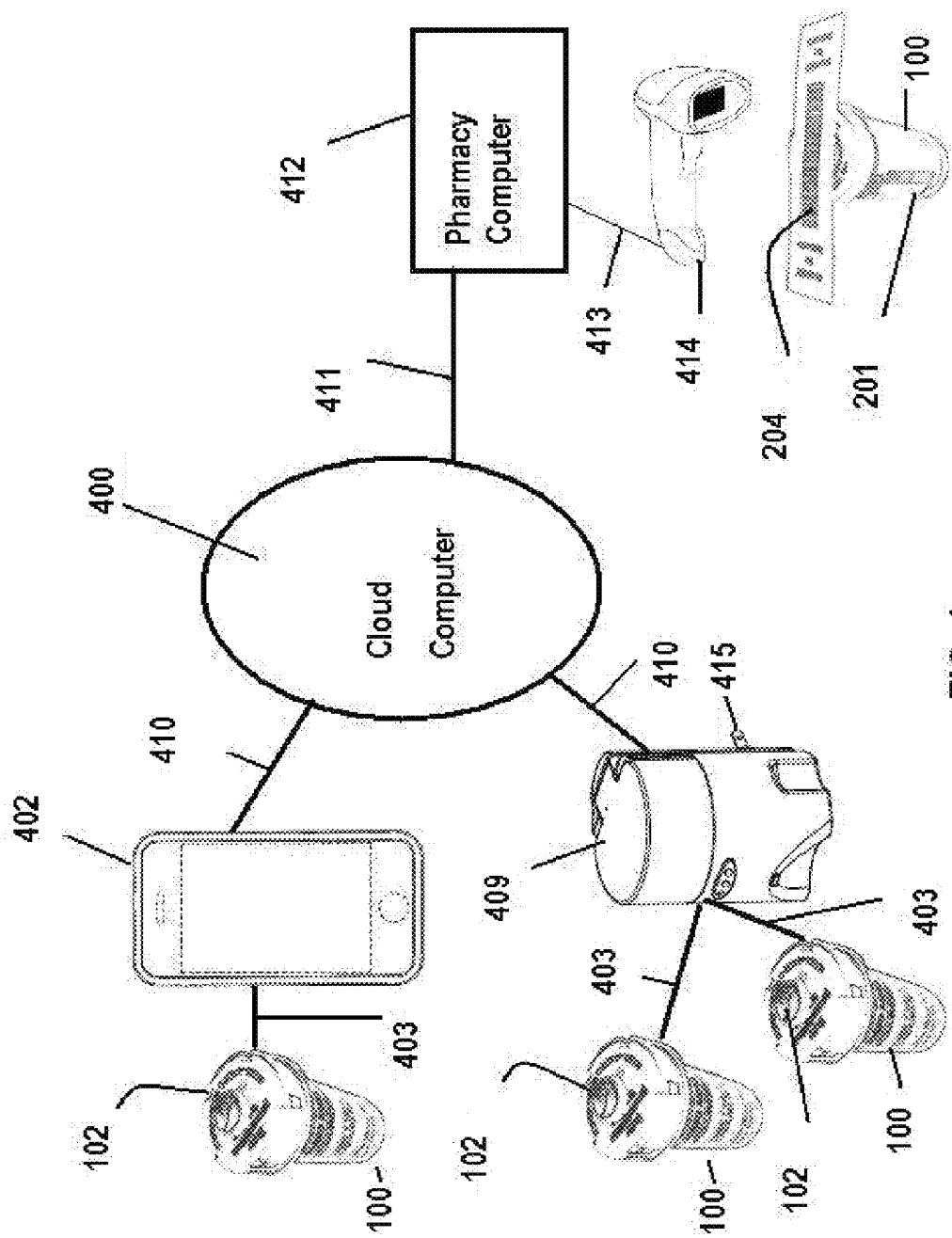
FIG. 4 depicts a system-level network diagram of certain embodiments of the invention.

FIG. 4 depicts a system-level network diagram of certain embodiments of the invention. Device 102 may communicate with mobile device 402 via wireless link 403. Mobile device 402 may be, but is not limited to, a smart phone, tablet, PDA, or the like. In a preferred embodiment, device 102 may communication with relay device 409 via wireless link 403. Relay device 409 has plug 415 to connect to a power source. Relay device 409 may contain any components known in the field to enable wireless communications with another device to transfer and receive data over a network. Mobile device 402 and relay device 409 are configured to communicate with cloud computer 400 via Internet 410. Cloud computer 400 is configured to communicate with a party of interest computer 412 via internet protocol 411. In one embodiment of the invention, computer 412 may be a pharmacy computer. In this embodiment, a pharmacist may use scanner 414 to input the data stored in barcodes 204 and 201 to party of interest computer 412 via link 413. It shall be appreciated that party of interest computer 412 may be any type of computing device known in the field such as a desktop computer, laptop, mobile device, or the like.

In operation, a pharmacist receives a user's prescription order from a physician. The prescription is filled in medication bottle 100. The pharmacist applies label 201 to medication bottle 100 and affixes the device 102 and paper strip 203 combination to medication cap 101 as shown in FIG. 2. The pharmacist then uses scanner 414 to scan the medication label barcode 201 and unique ID barcode 204 on paper strip 203. This scanned data from the barcodes are transferred to pharmacy computer 412 via link 413 and stored. Pharmacy computer 412 transmits the data to cloud computer 400 via internet protocol 411. Cloud computer 400 maintains a database, which stores all data received from pharmacy computer 412. As such, a file is created in the database for the user, which includes the unique ID of device 102, the patient's name, medication name and medication usage requirements. It shall be appreciated that the database in cloud computer 400 is configured to store a plurality of files in which each file corresponds to a different user/patient.

Paper strip 203 is removed from device 102 to activate the device before the medication bottle, medication cap and device are delivered to the user. Device 102 is now ready to track the medication use of the user. Every time the user opens or closes medication cap 101, SOC 301 of device 102 registers the time of such event. SOC 301 also monitors and records the amount of medication available in bottle 100 based on the number of times cap 101 is opened and closed. This medication use data is transmitted from device 102 to either mobile device 402 or relay device 409 via wireless link 403. Mobile device 402 or relay device 409 communicates the received medication use data over Internet 410 to cloud computer 400. Cloud computer 400 will constantly match the medication use data of each event with the user's corresponding file in the database. The pharmacist or any other party of interest, such as care-givers, nurses, doctors or family members, can use a computer 412 to access the user's file stored on cloud computer 400 via internet protocol 411. As such, any party of interest can review the user's file and track the user's medication use. This will allow the pharmacist to recognize when a user's medication needs to be refilled so there is no interruption in the medication use.

In one embodiment of the invention, cloud computer 400 determines whether the medication is consumed by the user at the intervals prescribed by the physician, and creates reports and/or alerts to persons of interest such as care-giver, nurses, doctors, family-member and pharmacists. In addition, cloud computer 400 may provide visual alerts to the user by activating light-emitting diode 312 on device 102 if it determines that the user is not consuming the medication at the frequency and/or quantity prescribed by the physician.

It shall be appreciated that the components of the system described in several embodiments herein may comprise alternative materials known in the field and be of any color, size and/or dimensions. It shall be appreciated that the components of the system described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A system for tracking the use of medication by a user in real-time, the system configured to generate data pertaining to the medication use including time of consumption and amount of medication available and transmit the data to a network so the data will be readily accessible to at least one party of interest, the system comprising:
a base unit housing configured to be affixed to a cover for use with a medication container, the base unit housing comprising a micro-electro-mechanical system configured to detect motion of the cover and determine when the user removes the cover from the medication container to permit a portion of medication stored therein to be dispensed, a computing device configured to generate the medication use data based on the removal of the cover from the medication container as determined by the micro-electro-mechanical system, and a communication system configured to transmit the medication use data to a cloud computer via the network, thereby providing the at least one party of interest access to the cloud computer and the medication use data.

2. The system of claim 1, wherein the base unit housing further comprises a plurality of apertures and a power source.

3. The system of claim 2, wherein the power source is a zinc-air battery.

4. The system of claim 3, wherein the base unit housing further comprises a layer affixed to the base unit such that the plurality of apertures on the base unit housing are sealed, wherein the zinc-air battery is configured to activate when the layer is removed from the base unit housing.

5. The system of claim 4, wherein the layer includes a barcode comprising identification data pertaining to the user.

6. The system of claim 5, wherein the communication system of the base unit housing transmits the medication use data to the cloud computer via a mobile device or a relay device.

7. The system of claim 5, further comprising at least one party of interest computing device operably connected to the cloud computer via the network.

8. The system of claim 5, further comprising an input device configured to transmit the user's identification data to the cloud computer via the network.

9. The system of claim 8, wherein the cloud computer is configured to store the medication use data and the user's identification data.

10. The system of claim 9, wherein the base unit further comprises a light-emitting diode configured to provide the user an alert pertaining to the medication use data.

11. A system for tracking the use of medication by a user in real-time, the system configured to generate data pertaining to the medication use including time of consumption and amount of medication available and transmit the data to a network so the data will be readily accessible to at least one party of interest, the system comprising:

a base unit housing configured to be affixed to a cover for use with a medication container, the base unit housing comprising a micro-electro-mechanical system configured to detect motion of the cover and determine when the user completely removes the cover from the medication container to permit a portion of medication stored therein to be dispensed, a computing device configured to generate the medication use data based on the complete removal of the cover from the medication container as determined by the micro-electro-mechanical system, and a communication system configured to transmit the medication use data to a cloud computer via the network, thereby providing the at least one party of interest access to the cloud computer and the medication use data.

* * * * *